(12) United States Patent
Becker et al.

(10) Patent No.: US 9,271,800 B2
(45) Date of Patent: Mar. 1, 2016

(54) MEDICAL DEVICE SYSTEM, MEDICAL DEVICE AND FLOOR-MOUNTED FRAME FOR A MEDICAL DEVICE

(71) Applicant: Dräger Medical GmbH, Lübeck (DE)

(72) Inventors: Uwe Becker, Eichenau (DE); Karsten Grest, Rehhorst (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 14/255,197

(22) Filed: Apr. 17, 2014

(65) Prior Publication Data

US 2014/0312192 A1  Oct. 23, 2014

(30) Foreign Application Priority Data

Apr. 18, 2013  (DE) .......................... 10 2013 006 700

(51) Int. Cl.
*F16M 13/00*  (2006.01)
*A61B 19/00*  (2006.01)

(52) U.S. Cl.
CPC ...................................... *A61B 19/26* (2013.01)

(58) Field of Classification Search
CPC ....................................................... A61B 19/26
USPC .............. 248/125.8, 129, 317, 320–322, 550, 248/647
See application file for complete search history.

(56) References Cited

U.S. PATENT DOCUMENTS

| 8,235,402 | B2 * | 8/2012 | Knappe et al. ............. 280/47.34 |
| 2004/0164220 | A1 * | 8/2004 | Newkirk ........................ 248/647 |
| 2006/0242763 | A1 * | 11/2006 | Graham et al. ................ 5/503.1 |
| 2008/0149788 | A1 * | 6/2008 | Wong et al. ................ 248/176.1 |

FOREIGN PATENT DOCUMENTS

DE    29614447 U1 * 10/1996
EP    0966944 A2 * 12/1999

* cited by examiner

*Primary Examiner* — Gwendolyn Baxter
(74) *Attorney, Agent, or Firm* — McGlew and Tuttle, P.C.

(57) ABSTRACT

A medical device (10), for use in an operating room, has a basic body (20) with a mechanical ceiling interface (22) for mounting on a mounting bracket (210) of a ceiling mounting system (200). The basic body (20) has a mechanical frame interface (24) for mounting on a floor-mounted frame (100).

17 Claims, 5 Drawing Sheets

MEDICAL DEVICE SYSTEM, MEDICAL DEVICE AND FLOOR-MOUNTED FRAME FOR A MEDICAL DEVICE

CROSS REFERENCE TO RELATED APPLICATIONS

This application claims the benefit of priority under 35 U.S.C. §119 of German Patent Application DE 10 2013 006 700.6 filed Apr. 18, 2103, the entire contents of which are incorporated herein by reference.

FIELD OF THE INVENTION

The present invention pertains to a medical device for use in an operating room, to a floor-mounted frame for supporting such a medical device, to a medical device system, having a medical device and a floor-mounted frame, as well as to a method for converting a ceiling-mounted medical device into a medical device system.

BACKGROUND OF THE INVENTION

It is known, in principle, that medical devices may be used in various use situations. These are especially the floor-mounted mode of use and the ceiling-mounted mode of use in an operating room. For example, floor-mounted and movable frames are known, on which the medical devices are arranged and thus can be moved about in the operating room. Further, it is known that ceiling suspension systems, to which the medical devices can be fastened, are present in operating rooms. Thus, such ceiling-mounting systems often have a mounting bracket, on which a mechanical connection can be made available at a corresponding interface of the medical device. The media supply, e.g., with medical gases, is also known via such interfaces.

The drawback of prior-art solutions is that the frame remains at the medical device in case of conversion from a floor-mounted device into a ceiling-mounted device. Thus, the medical device is pushed with the movable frame into the operating room in prior-art solutions and a mechanical connection is established there between the ceiling interface and the mounting bracket of the ceiling mounting system. The medical device with the floor-mounted frame can be subsequently raised via the mounting bracket. This leads to an additional need for installation space for the entire medical device system. It is possible, in particular, that the frame of the medical device gets disturbingly caught, so to speak, in the area of the operating room. Carrying out maintenance on the medical device is very complicated in prior-art solutions in which a floor-mounted frame is eliminated. Since such devices usually have a weight of up to 100 kg and more, this leads to several people being required to remove the medical device from the mounting bracket of the ceiling mounting system. The ceiling mounting system can correspondingly be removed and then moved into a service room with great effort only.

SUMMARY OF THE INVENTION

An object of the present invention is to at least partly eliminate the above-described drawbacks. An object of the present invention is, in particular, to make available a variation between a floor-mounted intended use and a ceiling-mounted intended use of one and the same medical device in a cost-effective and simple manner.

The above object is accomplished by a medical device according to the invention, by a floor-mounted frame according to the invention, by a medical device system according to the invention, as well as a method according to the invention. Features and details that are described in connection with the medical device according to the present invention also apply, of course, in connection with the floor-mounted frame according to the present invention, with the medical device system according to the present invention as well as with the method according to the present invention and each vice versa, so that reference is or can always be reciprocally made concerning the disclosure to the individual aspects of the present invention.

A medical device according to the present invention is intended for use in an operating room and has a basic body. A mechanical ceiling interface is provided on this basic body for fastening to a mounting bracket of a ceiling mounting system. The ceiling interface of the basic body connects to a device interface of the mounting bracket of the ceiling mounting system. A medical device according to the present invention is characterized in that the basic body has, further, a mechanical frame interface for fastening to a floor-mounted frame. The design of a medical device according to the present invention is consequently based on already known medical devices, which are designed for being fastened to a ceiling mounting system. The mechanical ceiling interface is correspondingly designed in the known manner and correspondingly corresponds to already existing, prior-art ceiling mounting systems. The ceiling interface of the basic body connects to a device interface of the mounting bracket of the ceiling mounting system. It thus becomes possible that a medical device according to the present invention also continues to be able to be used on already installed ceiling mounting systems in operating rooms. The definition of a ceiling mounting system also covers (also includes) other systems, especially wall mounting systems, in the sense of the present invention.

The essence of the present invention is to create an additional mechanical interface, which is designed as a mechanical frame interface in this case. The mechanical frame interface is thus designed for fastening to the floor-mounted frame separately from the mechanical ceiling interface. This causes that two use situations are defined for the medical device via the two separate mechanical interfaces. On the one hand, a mounting bracket of a ceiling mounting system can be connected and fastened via the mechanical ceiling interface. On the other hand, it is possible to make available a correlation with a floor-mounted frame and hence fastening of same for a floor-mounted use situation.

Fastening to the respective system may also be carried out separately due to the separation of the two mechanical interfaces from one another. In particular, a changeover between the two use situations is possible in an especially simple manner and above all rapidly and in a cost-effective manner.

If, e.g., the medical device is located in a use situation in which, the medical device is arranged in the operating room movably on the floor-mounted frame, the mounting bracket can be coupled with and fastened to this interface via the ceiling interface, while the medical device is still fastened to the floor-mounted frame via the mechanical frame interface. After fastening to the ceiling interface, the mechanical frame interface can be disconnected, so that the medical device is raised from the mounting bracket without the floor-mounted frame. The floor-mounted frame, which is no longer needed now, can be stored away and especially removed from the operating room. Compared to prior-art systems, the medical device is now reduced concerning the necessary installation space within the operating room.

If it is desirable to change a use situation in the reverse order or if maintenance must be performed on a medical device in the situation in which the medical device is used in the ceiling-mounted situation, a floor-mounted frame is made available and moved into a changeover position. The medical device is lowered via the fastening bracket and placed above the floor-mounted frame. The mechanical frame interface is subsequently used for fastening to the floor-mounted frame, so that the medical device is again connected by both interfaces with the respective corresponding component for this intermediate phase. The mechanical ceiling interface is then detached, so that the mounting bracket can again be moved into an inoperative position. The medical device is now still fastened to the floor-mounted frame via the mechanical frame interface and can be used freely in the operating room as a floor-mounted use situation. It is also possible to move the medical device out of the operating room, e.g., into a maintenance room, in order to carry out a basic maintenance of the device.

An operating room is defined in the sense of the present invention especially as a room of a hospital. However, it may also cover any other treatment room which is present in hospitals or in medical offices. Patient rooms, which shall be equipped with additional treatment systems, may also be covered by the definition of an operating room in the sense of the present invention.

The medical device may have features of any known medical device. The medical device may include operating room lights (with one or more illuminants), a respirator (also known as ventilator) system or an anesthesia system, a liquid anesthetic feed system, monitoring devices, monitoring sensor connections, patient monitors and displays.

In the sense of the present invention, the basic body is especially a support frame and/or a housing of the medical device. The two mechanical interfaces are consequently accessible preferably from the outside of the medical device, and, in particular, the two mechanical interfaces are visible without removal of cover elements and can also be used for the corresponding fastening to the corresponding component.

A floor-mounted frame may be an upright and/or movable, especially rollable frame. The floor-mounted use situation is associated especially with correspondingly movable floor-mounted frames to make it possible to guarantee the possibility of free arrangement along the floor surface for the medical device in the floor use situation.

The different interfaces, especially the ceiling interface, are preferably additionally provided with media interfaces, which are used for the supply with media. Thus, a ceiling mounting system may also make available, in addition to the mechanical mounting, media in the form of electricity, air or other gases, especially from a hospital network. It is thus advantageous if a correlation with such a hospital network is also made available via the mechanical ceiling interface via the ceiling mounting system and correspondingly also via the mechanical ceiling interface.

A fastening, especially between the mechanical frame interface and the floor-mounted frame, is not necessarily defined as a fixation, but such a fixation may be advantageous. Fastening is brought about in such a manner that especially tilting or falling off of the medical device from the floor-mounted frame is avoided after establishing the fastening for the expected intended uses. In particular, tilting is to be avoided during a motion even over slanting ramps of up to about 5° or over door sills. Due to the heavy weight of the medical device, simple placing and a combination, e.g., with a tilt preventing means as a tilt-resisting fastening may correspondingly already represent a fastening in the sense of the present invention. Such a fastening does not consequently rule out the possibility of lifting off the medical device upwardly without a corresponding mechanical fixation.

The individual mechanical interfaces are designed especially for a statically determined mounting. Thus, fastening is correspondingly defined as a possibility of transmitting forces for the bearing forces. As this was already explained, the corresponding interface is correlated, in particular, with a fixing means, which is a part of the interface, in order to also make it possible to provide a fixation for the statically determined mounting, besides the fastening.

As was also already explained above, the interfaces are designed as reversible interfaces in order to make it possible to change over as desired between the described intended uses. The mounting on and removal from the corresponding interface are preferably carried out without tools.

It is advantageous if the frame interface has fixing means for fixing the basic body on the frame in a defined relative position in a medical device according to the present invention. As was discussed in detail above, the fixing means is a further form of fastening in this case. For example, hook-like elements may thus be provided, which grip behind corresponding mounting openings in order to make it possible to guarantee the fixation of the medical device on the basic body or on the frame. The relative arrangement is irrelevant in this case. Thus, the movable hooks may be provided on the medical device or on the frame and the mounting openings, behind which said hooks can grip, may be correspondingly provided on the frame or on the medical device. Only the functional correlation of the fixing means is important for bringing about the fixing function. The fixing means on the device preferably correspond to opposite fixing means of a fixing device on the frame. For example, a snap locking functionality is also conceivable for the fixing means to make it possible to guarantee the fixation when bringing the medical device and the frame together in an even simpler manner and so-to-speak automatically. Compared to a simple fastening, fixation causes the medical device not to be able to be lifted off from the frame any longer without detaching the fixing means. If an attempt is made, in case of fixation by means of fixing means, to raise the medical device, it will be raised together with the frame fixed thereto. The provision of fixing means correspondingly leads to additional securing for the mechanical stability of a medical system manufactured in this manner.

It may likewise be advantageous if the basic body, especially the frame interface, has a guide means with at least one guide element, which guides the basic body into a defined relative position while the basic body is being placed on the frame. A defined relative position must be made available for the correlation between the frame and the frame interface of the basic body of the medical device especially when changing over from the ceiling-mounted use situation to a floor-mounted use situation. Thus, the last relative positioning is preferably carried out by means of the guide means. Such a guide means is used to make it possible to make available the defined relative position for an accurate mechanical correlation of the interfaces of the device and of the frame during the motion of the medical device towards the frame. In particular, the guide means of the medical device cooperates with opposite guide means of the frame, so that, on the whole, a guiding device is formed for the medical device system. Grasping manually under the medical device or viewing of the medical device from below is no longer necessary in this embodiment for aligning the device with the frame. The relative positioning and hence the subsequent necessary correlation between the two interfaces of the frame and of the device can thus be achieved markedly more rapidly, in a more cost-effective manner and above with a higher level of safety.

It may likewise be advantageous if the at least one guide element of the guide means in the medical device according to the present invention has a guiding surface, which forms an acute angle with the direction of mounting for a relative positioning of the basic body relative to the frame. The direction of mounting is preferably directed from top to bottom, i.e., the direction of mounting corresponds to the direction for putting down the medical device on the frame. An arrangement at acute angles of the corresponding guiding surface of the guide means serves the purpose of automatically generating a relative motion when putting down. If, for example, the medical device is put down slowly via a mounting bracket in the ceiling-mounted use situation, a frame mounted on rollers can be moved and displaced relative to the medical device via the guiding surface until the frame will reach the defined relative position for the correlation of the two interfaces. This leads to an even easier generation of the defined relative position and hence to a further increase in safety regarding the necessary correlation of the interfaces. A range of less than about 45° and especially less than about 20° is preferred for the acute angle. The guiding surface preferably corresponds to an opposite guiding surface of the frame.

It is likewise advantageous, furthermore, if the basic body in a medical device according to the present invention has a sensor means comprising at least one sensor, which recognizes the state of fastening of the frame interface at a frame and/or of the ceiling interface at a mounting bracket. Such sensor means are especially electronic in nature and can recognize the actual state of fastening of the interfaces by means of a great variety of sensor functionalities, e.g., by induction, a change in resistance, magnetism or other physical effects, e.g., by means of photoelectric cells. This leads to a greater safety in the use of a medical device. In particular, it can be ensured that the ceiling interface is detached only when the frame is fastened to the frame interface. It can thus be ensured that an unintended detaching of the ceiling interface, which would lead to the medical device falling down in an undesired manner, is avoided. The sensor means is correlated especially with a control unit and make the corresponding data available to same. The operability of the overall system is thus improved and safety is increased. Besides the fastening situation of the two interfaces, a fixing means can be monitored as well. It can be ensured that the fixing element of the fixing means is not closed already before the medical device has been placed on the frame.

The present invention also pertains to a floor-mounted frame, having a stand means for being set up on the floor surface and a basic body with a device interface for fastening a medical device according to the present invention. A floor-mounted frame thus brings the same advantages with it as they were explained in detail in reference to a medical device according to the present invention. The stand means is especially a rollable stand. The stand means or stand may also be designed as stationary stand. The stand means may also comprise sliding mounts. Such a floor-mounted frame may be designed as a permanent frame for a longer period of use in an operating room. However, it is also possible that the floor-mounted frame is designed as a service cart exclusively for briefly moving the medical device, e.g., into a maintenance room.

The floor-mounted frame according to the present invention can be varied in such a way that the frame body, especially the device interface, has opposite fixing means for fixing the basic body of the medical device on the frame in a defined relative position. The same advantages are thus obtained as those explained in detail in reference to the fixing means used as a fixing device with the opposite fixing means for the medical device.

Further, it is advantageous if the frame body, especially the device interface, in a floor-mounted frame according to the present invention has at least one opposite guide means, which guides the basic body into a defined relative position while the basic body of the medical device is being placed on the frame. The same advantages are also obtained in this case as those that were explained in detail with reference to the guide means of a medical device according to the present invention. Opposite guide means and guide means consequently form the above-mentioned guiding device in this case.

It may be advantageous in case of a floor-mounted frame according to the above paragraph if the at least one guide element of the opposite guide means has an opposite guiding surface, which forms an acute angle with the direction of mounting for the relative positioning of the basic body of the medical device in relation to the frame. Reference is made here once again to the guide means with the guiding surface with reference to a medical device, because the same advantages can be obtained in this case. The guide elements of the opposite guide means have an opposite guiding surface, which preferably likewise forms an acute angle of less than about 45° and preferably less than about 20° with the direction of mounting. The angles of the opposite guiding surface and the guiding surface of a common guiding device are preferably quasi adapted to one another and are correlated, and the angles of the opposite guiding surface and the guiding surface have especially an identical or essentially identical design.

It is likewise advantageous if the at least one guide element of the opposite guiding means in a floor-mounted frame according to the present invention is designed as a guide plate, which cooperates with at least one outer side of the basic body of the medical device as a guiding surface. Thus, such a guide plate may be designed as an opposite guide means, e.g., in an L-shaped or U-shaped form in the top view of the floor-mounted frame. If the medical device is now lowered, the floor-mounted frame can be placed or moved by means of the guide plate such that it will more or less enclose the outer side of the basic body of the medical device and the necessary relative positioning can thus take place. It is subsequently possible that fixing means will additionally used to grip behind the basic body in relation to the opposite guide means.

It is likewise advantageous if the opposite guide means comprises at least one opposite guide element that is designed in the floor-mounted frame according to the present invention as a three-dimensional geometric body, especially as a spherical segment and/or as a conical segment, which guides the medical device into a defined relative position with a corresponding guide means of the medical device in question. This is an alternative embodiment of the opposite guide means. Conical segments or spherical segments already have guiding surfaces, which have a corresponding angular orientation in relation to the direction of mounting. An even more greatly facilitated relative positioning is made available in this case by three-dimensional geometric bodies, especially ones of a rotationally symmetrical design. Securing against tilting is preferably also achieved in this case, in addition, which may make it possible to do away with fixing means.

A further advantage is obtained if the at least one opposite guide means in a floor-mounted frame according to the present invention is designed as a guide pin, which guides the medical device into a defined relative position with a corresponding guide means of the medical device in question. In particular, two or more guide pins are provided in order to make available the defined relative position in any desired orientation. The pins mesh, e.g., with corresponding guide openings of the guide means of the medical device and can slide along there on guiding surfaces. The lead-in bevel is used in this case as an opposite guiding surface, e.g., to facilitate the insertion of the guide means, in order to facilitate the guiding even more for generating the defined relative position.

The present invention also pertains to a medical device system, having a medical device according to the present invention as well as a floor-mounted frame according to the present invention, wherein the medical device is fastened to the device interface of the frame by means of the frame interface. A medical device system correspondingly brings with it the same advantages as those explained in detail with reference to a floor-mounted frame and a medical device according to the present invention. The individual components separately or the medical device system as a whole may be provided as a commercially available unit.

The present invention also pertains to a method for converting a ceiling-mounted medical device, especially one according to the present invention, into a floor-mounted medical device system, especially one according to the present invention, having the following steps:

Lowering of the medical device by means of a mounting bracket of a ceiling mounting system, which said bracket is fastened to a ceiling interface of the medical device, prepositioning of a floor-mounted frame, especially one according to the present invention, under the medical device, alignment of the frame and of the medical device, especially by means of guide means and/or opposite guide means, into a defined relative position, and mounting of a medical device by means of a frame interface on a device interface of the frame, and detaching of the mounting bracket from the ceiling interface.

It is, of course, also possible to use additional steps in a method according to the present invention. It shall also be pointed out that a reversed order of the steps for changing over from a floor-mounted use situation to a ceiling-mounted use situation is also possible. The use of a sensor means is also possible to ensure that the order of connection or fastening with/to the individual mechanical interfaces takes place in the correct order. The provision of a fixing means and the closure of such fixing means are also conceivable in the sense of the present invention.

It should be pointed out, in principle, that especially with reference to the fixing means described and also with reference to the guide means described, arrangement is possible, of course, in both directions. Thus, the opposite guide means described may, of course, also be designed in the same manner as guide means on the medical device, so that the same functionality is obtained by a simple kinematic reversal of the embodiments described. Such kinematic reversals are, of course, also within the scope of the present invention.

Further advantages, features and details of the present invention appear from the following description, in which exemplary embodiments of the present invention are described specifically with reference to the drawings. The features mentioned in the claims and in the description may be essential for the present invention both individually or in any combination. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
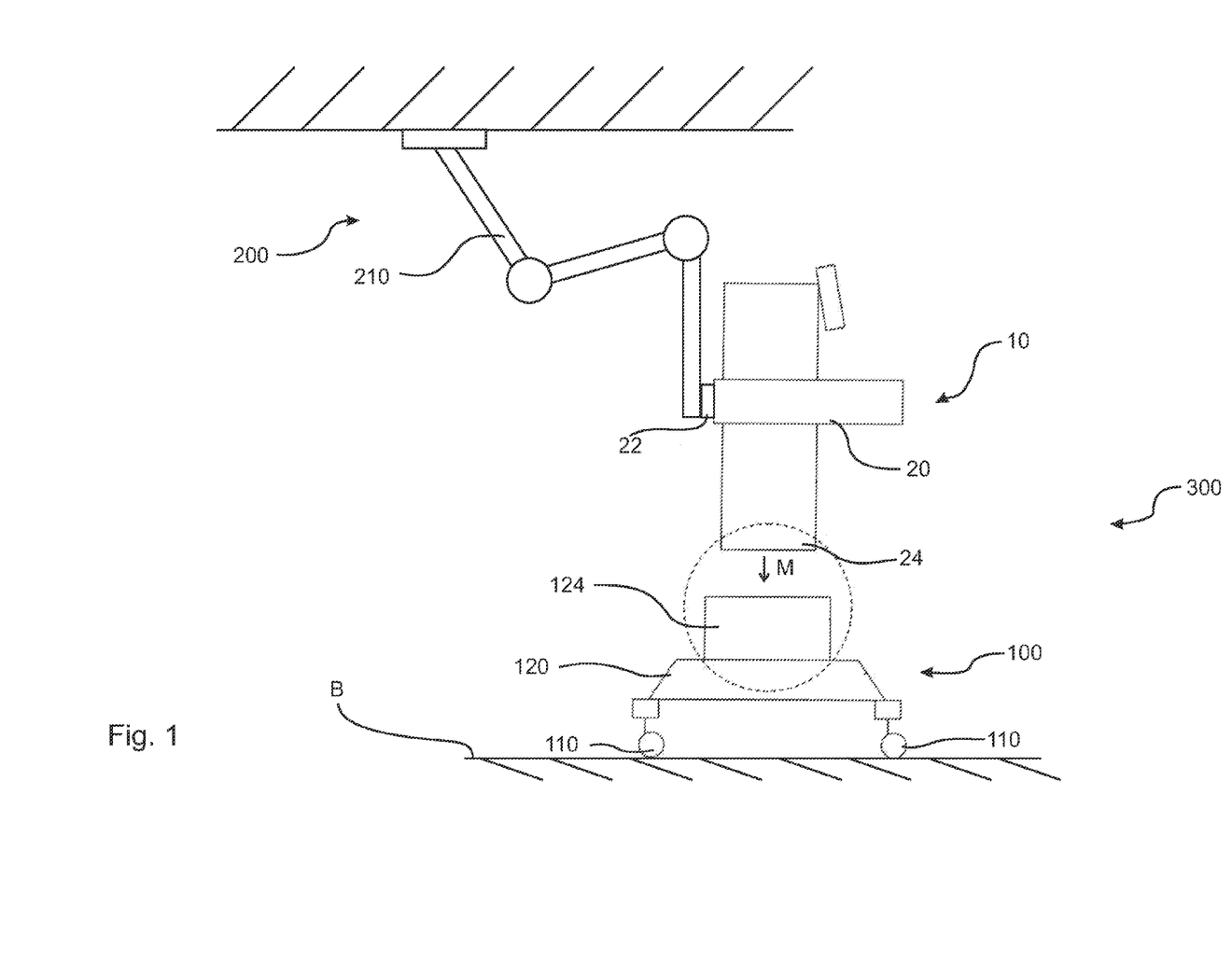
FIG. 1 is a schematic view showing a first embodiment of a medical device system according to the present invention.

Referring to the drawings in particular, FIG. 1 generally shows the overall situation for a medical device system 300 according to the present invention. A medical device 10 is located in a ceiling-mounted use situation in this case and shall be changed over from this ceiling-mounted use situation to a floor-mounted use situation.

The medical device 10 is mounted by means of a ceiling interface 22 on a mounting bracket 210 of a ceiling mounting system 200. The ceiling interface 22 of the basic body provides a connection to a medical device interface of the mounting bracket 210 of the ceiling mounting system 200. The ceiling interface 22 and the medical device interface connection provide a fastening of the medical device 10 to the bracket 210. The ceiling interface 22 and the medical device interface connection includes a fixing device (with at least one bracket side fixing feature and at least one opposite side fixing feature) to fix and mount the medical device 10 to the bracket 210. The ceiling interface 22 and the medical device interface connection may include a guiding device (with at least one bracket side guiding feature and at least one opposite side guiding feature) to guide the ceiling interface relative to the device interface and to assist with positioning the ceiling interface 22 relative to the device interface as the medical device 10 is connected to the mounting bracket 210. The ceiling interface 22 and device interface may provide media supply connections such as connections to supply electricity, air, $O_2$, laughing gas and gas or liquid anesthetic from the ceiling mounting system 200 to the medical device 10 as well as to provide signal, sensor, data and communications connections between the ceiling mounting system 200 to the medical device 10.

To convert the medical device 10 mounted state with the ceiling mounting system 200 to the floor-mounted use state (situation), a floor-mounted frame 100 is provided that is placed under the medical device. The floor-mounted frame has stand means comprising a stand 110 in the form of rollers for such a placement. A device interface 124 is formed on the frame body 120 of the floor-mounted frame 100. The medical device can now be lowered slowly in the direction of mounting M in the relative positioning, as it is shown in FIG. 1, by means of the mounting bracket 210. Guide means 28 and opposite guide means 128, not yet shown in greater detail, are used for a fine relative positioning of the medical device 10 and the floor-mounted frame 100 in relation to one another. After lowering and correlating the frame interface 24 and the device interface 124, the mounting bracket 210 can be detached from the ceiling interface 22 and the mounting bracket 210 moves into an inoperative position. The medical device system 300 is a floor-mounted medical device 10 now.

Figure 2:
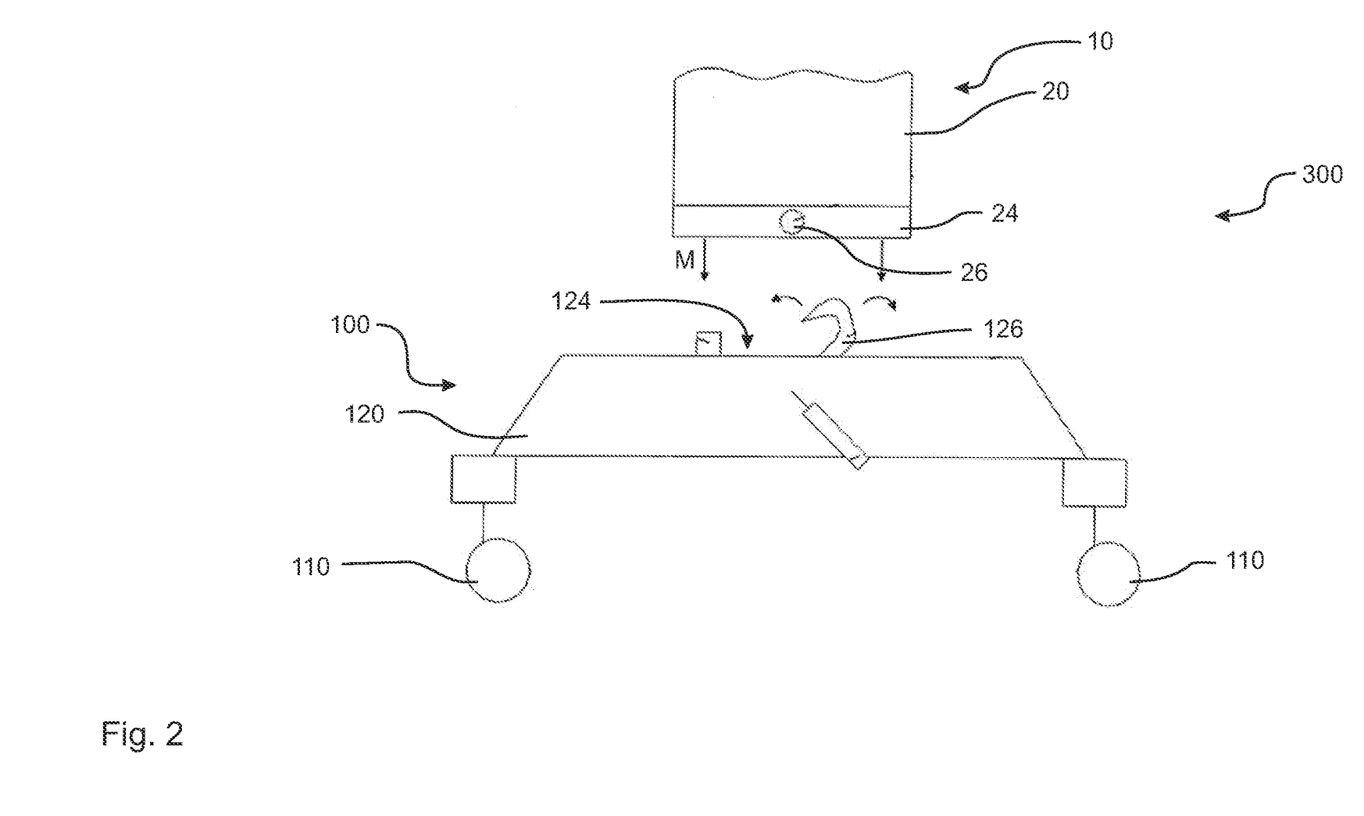
FIG. 2 is a schematic view showing an embodiment of a fixing means.

FIG. 2 shows a possibility of additional fixation for fastening. An opposite fixing means (or complementary fixing means or complementary fixing arrangement) 126 comprises a hook-shaped element, provided in this case on the floor-mounted frame 100 in the area of the device interface 124. A bolt, which can be gripped from behind, is provided as a fixing means 26 at the frame interface 24 on the basic body 20 of the medical device. After fastening in the direction of mounting M, the opposite fixing means 126 is moved, so that the hook grips behind the bolt of the fixing means 26. An additional securing against tilting is brought about by an additional fixation besides a simple placement as a fastening.

Figure 3:
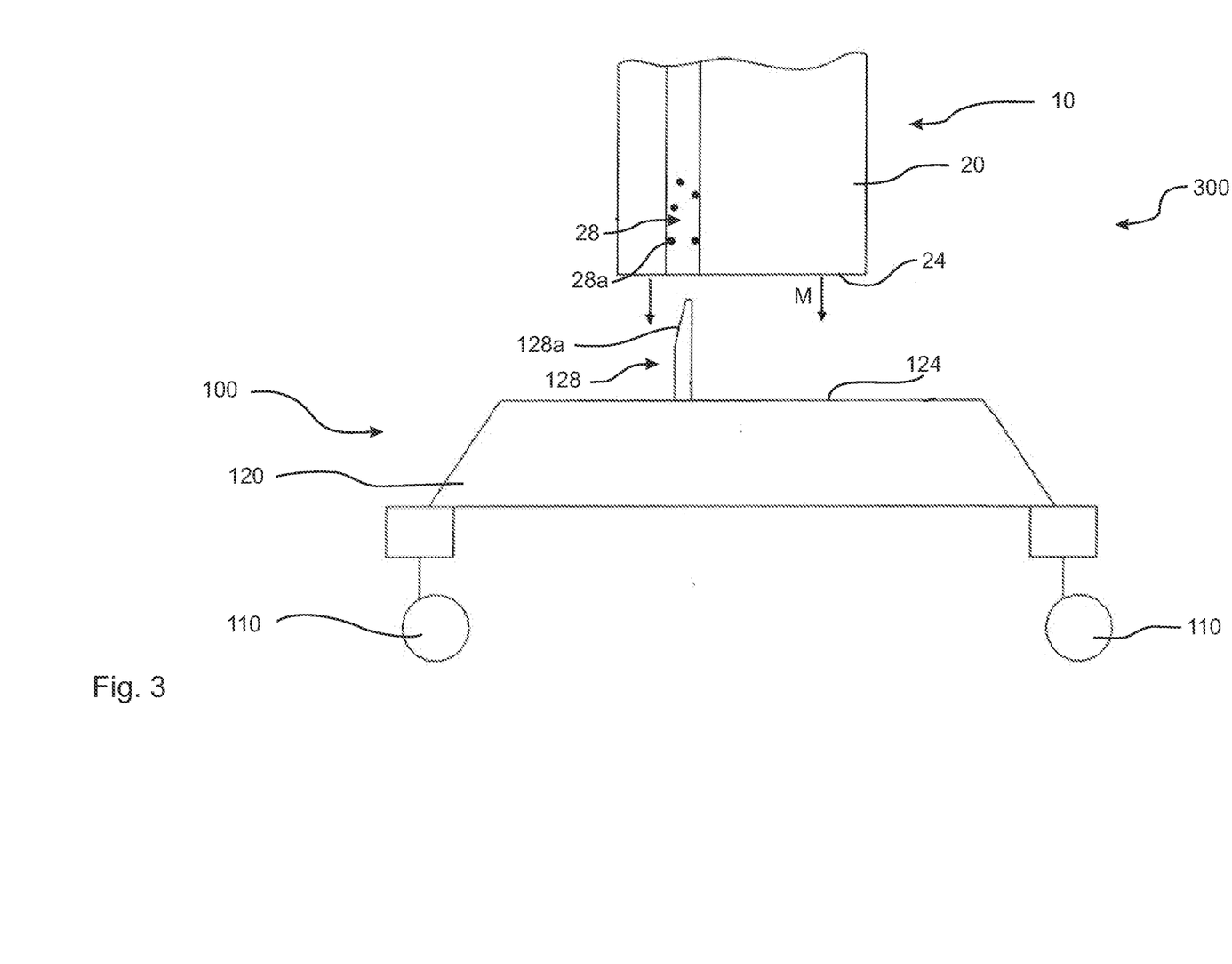
FIG. 3 is a schematic view showing a first embodiment of a guide means.

FIG. 3 shows a possible embodiment of a correlation of guide means 28 and opposite guide means 128. A guide pin is provided as an opposite guide means 128 in the area of the device interface 124. This guide pin has, in its topmost section, an opposite guiding surface 128a, which forms an acute angle with the direction of mounting M. Individual pins, which have guiding surfaces 28a, which likewise form acute angles with the direction of mounting M, are arranged in a guiding opening of a guide means 28. When the guide pin as an opposite guide means 128 is inserted into the guide means 28, the medical device 10 is aligned with the floor-mounted frame 100 in a defined manner, so that, for example, a define relative position can be subsequently obtained for carrying out a fixation by means of fixing means, as is shown, e.g., in FIG. 2.

Figure 4:
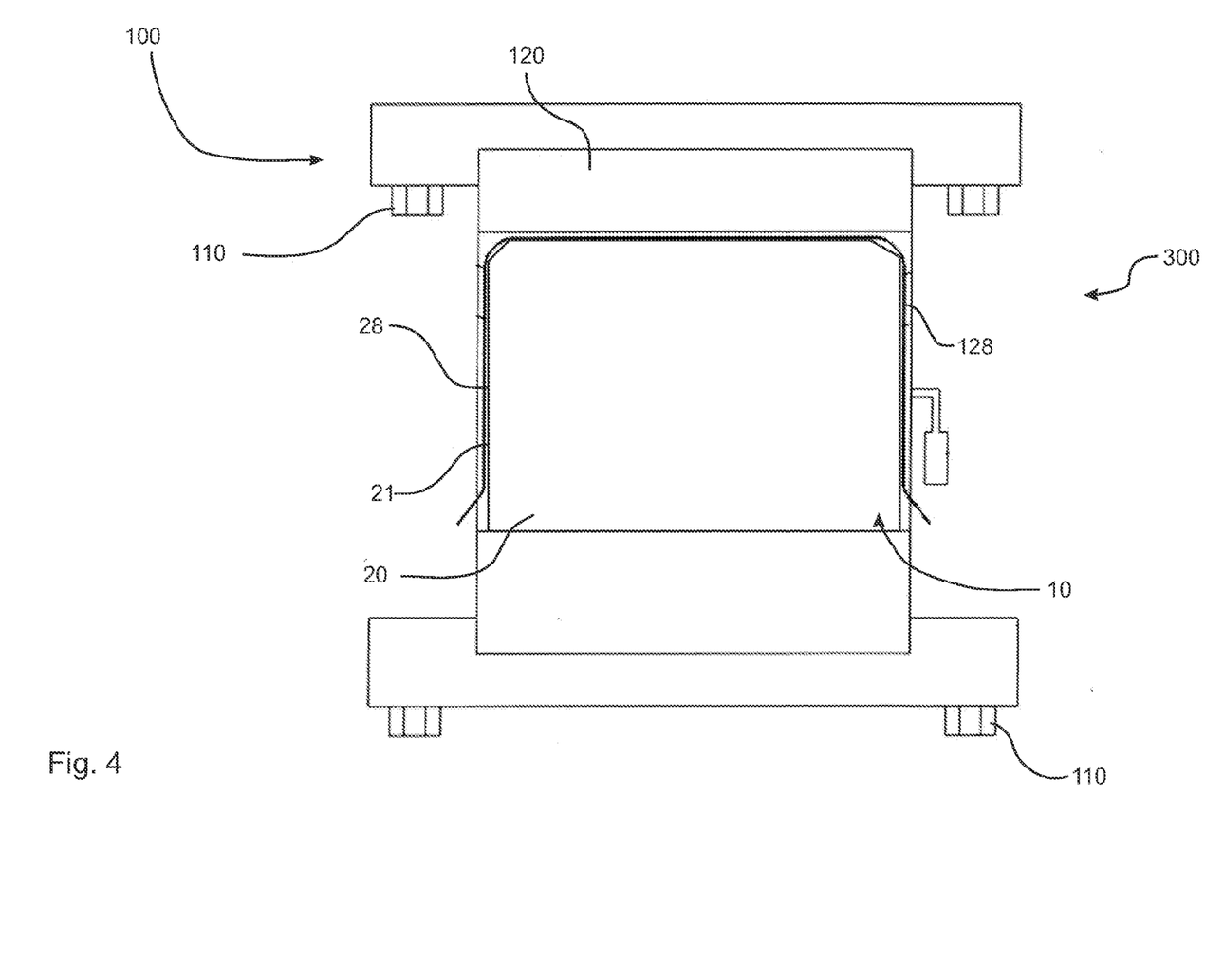
FIG. 4 is a schematic view showing another embodiment of a guide means.

FIG. 4 shows another embodiment of a design of the opposite guide means 128 according to the present invention. This is a guide plate, which is bent in a U-shaped form and surrounds the outer side 21 from the outside as a guide means 289 of the basic body 20 of the medical device 10. An easier relative positioning, which is, above all, visible from the outside, will follow in this case and it will facilitate the subsequent fixation even more.

Figure 5:
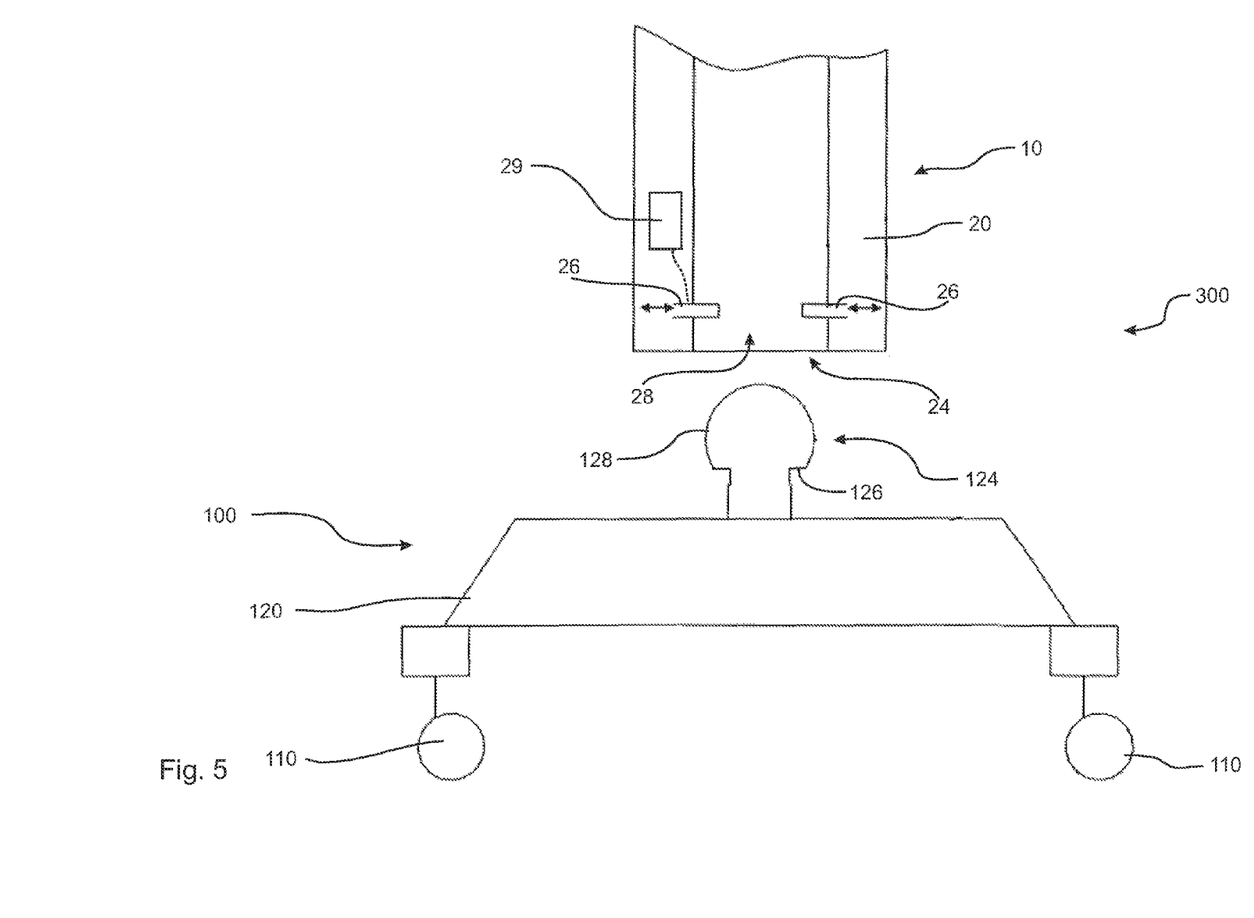
FIG. 5 is a schematic view showing another embodiment of a guide means.

FIG. 5 also shows an embodiment of an opposite guide means 128. This is designed as a geometric body in this case, which may also have a conical design besides the spherical shape shown. In particular, the opposite guide means 128 has a rotationally symmetrical design. During placement, the opposite guide means 128 penetrates into a corresponding guiding opening acting as a guide means 28 of the medical device 10. Guiding and hence relative positioning of the two components in relation to one another is carried out during the penetration. It can be recognized in this case as well that fixing means 26 are provided for gripping behind opposite fixing means 126 of the spherical head. The possibility of motion of the fixing means 26 is shown along the double arrows. It can, moreover, be recognized in this embodiment that sensor means 29 can recognize the fastening situation of the fixing means 26. These sensor means 29 cooperate especially with a control unit, so that it can be ensured that the ceiling interface 22 can detach from the mounting bracket 210 only after the fixing means 26 have been closed. It is thus ensured that the medical device is detached from the mechanical mounting on the mounting bracket 210 only after it stands securely on the floor surface B.

The above explanation of the embodiments describes the present invention exclusively within the framework of examples. Individual features of the embodiments, insofar as technically meaningful, may, of course, be freely combined with one another without going beyond the scope of the present invention.

While specific embodiments of the invention have been shown and described in detail to illustrate the application of the principles of the invention, it will be understood that the invention may be embodied otherwise without departing from such principles.

APPENDIX

10 Medical device
20 Basic body
21 Outer side
22 Ceiling interface
24 Frame interface
26 Fixing means
28 Guide means
28a Guiding surface
29 Sensor means
100 Floor-mounted frame
110 Stand means
120 Frame body
124 Device interface
126 Opposite fixing means
128 Opposite guide means
128a Opposite guiding surface
200 Ceiling mounting system
210 Mounting bracket
300 Medical device system
M Direction of mounting
B Floor surface

What is claimed is:

1. A medical device for use in an operating room, the medical device comprising:
   a basic body;
   a mechanical ceiling interface for mounting on a mounting bracket of a ceiling mounting system, the mechanical ceiling interface being connected to the basic body; and
   a mechanical frame interface for mounting on a floor-mounted frame, the mechanical frame interface being connected to the basic body, the basic body including at least a sensor means for recognizing at least one of a state of mounting of the frame interface on the frame and a state of mounting of the ceiling interface on the mounting bracket.

2. A medical device in accordance with claim 1, wherein the frame interface comprises fixing means for fixing the basic body on the frame in a defined relative position.

3. A medical device in accordance with claim 1, further comprising a guide means for guiding the basic body into a defined position relative to the frame, the guide means being connected to at least one of the frame interface and the basic body, wherein the basic body is guided into the defined position while the basic body is being placed on the frame.

4. A medical device in accordance with claim 3, wherein the guide means comprises at least one guide element with a guiding surface, the guiding surface forming an acute angle with respect to a direction of mounting, whereby the guiding surface provides a relative positioning of the basic body relative to the frame.

5. A floor-mounted frame comprising:
   a stand providing support on a floor surface;
   a frame body connected to the stand; and
   a device interface for fastening a medical device comprising a basic body, a mechanical ceiling interface for mounting on a mounting bracket of a ceiling mounting system, the mechanical ceiling interface being connected to the basic body and a mechanical frame interface for mounting on the floor-mounted frame, the mechanical frame interface being connected to the basic body for connection to the device interface, the basic body including at least a sensor means for recognizing at least one of a state of mounting of the frame interface on the frame and a state of mounting of the ceiling interface on the mounting bracket.

6. A floor-mounted frame in accordance with claim 5, further comprising an opposite fixing means for fixing the basic body of the medical device on the frame in a defined relative position, the opposite fixing means being connected to at least one of the frame body and the device interface.

7. A floor-mounted frame in accordance with claim 5, further comprising an opposite guide means for guiding the basic body into a defined position relative to the frame while the basic body of the medical device is being placed on the frame, wherein the opposite guide means is connected to at last one of the frame body and the device interface.

8. A floor-mounted frame in accordance with claim 7, wherein the opposite guide means comprises an opposite guiding surface, which forms an acute angle with a direction of mounting for a relative positioning of the basic body of the medical device relative to the frame.

9. A floor-mounted frame in accordance with claim 7, wherein the opposite guide means comprises a guide plate, which cooperates with at least one outer side of the basic body of the medical device, which at least one outer side of the basic body forms a guiding surface.

10. A floor-mounted frame in accordance with claim 7, wherein the opposite guide means comprises a three-dimensional geometric body formed as one of a spherical segment and a conical segment, the three-dimensional geometric body guiding the medical device into a defined relative position with a corresponding guide means of the medical device in question.

11. A floor-mounted frame in accordance with claim 7, wherein the opposite guide means comprises a guide pin, which moves the medical device into a defined relative position with a corresponding guide means of the medical device in question.

12. A medical device system comprising:
a ceiling mounting system;
a floor-mounted frame comprising a stand providing support on a floor surface, a frame body connected to said stand;
a basic body with a ceiling interface for mounting said basic body on said ceiling mounting system, said basic body including a floor frame interface for mounting said basic body on said floor-mounted frame;
a sensor means for sensing a mounting of said floor frame interface on said floor-mounted frame, said sensor means also sensing a mounting of said ceiling interface on said ceiling mounting system.

13. A medical device system in accordance with claim 12, wherein floor frame interface comprises fixing means for fixing said basic body on said floor-mounted frame in a defined relative position.

14. A medical device system in accordance with claim 12, further comprising a guide means for guiding the basic body into a defined position relative to the floor-mounted frame, the guide means being connected to at least one of the floor-mounted frame and the basic body, wherein the basic body is guided into the defined position while the basic body is being placed on the floor-mounted frame.

15. A medical device system in accordance with claim 12, further comprising an opposite fixing means for fixing the basic body of the medical device on the floor-mounted frame in a defined relative position, the opposite fixing means being connected to at least one of the floor-mounted frame body and the floor frame interface.

16. A medical device system in accordance with claim 12, further comprising an opposite guide means for guiding the basic body into a defined position relative to the floor-mounted frame while the basic body of the medical device is being placed on the floor-mounted frame, wherein the opposite guide means is connected to at last one of the frame body and the floor frame interface.

17. A medical device system comprising:
a ceiling mounting system with a mounting bracket;
a floor-mounted frame comprising a stand providing support on a floor surface, a frame body connected to said stand and a device interface
a basic body with a ceiling interface for mounting said basic body on said ceiling mounting system, said basic body including a floor frame interface for mounting said basic body on said floor-mounted frame;
a guide arranged on said floor-mounted frame, said guide guiding said basic body into a defined position relative to said floor-mounted frame when said basic body is placed on said floor-mounted frame, said guide includes a guide plate having one of an L-shaped and U-shaped form in a top view of said floor-mounted frame, said guide plate being adapted such that it will guide an outer side of said basic body of the medical device into said defined position relative to said floor-mounted frame.

* * * * *